(12) United States Patent
Shimizu

(10) Patent No.: US 6,589,511 B1
(45) Date of Patent: Jul. 8, 2003

(54) COMPOSITION FOR FORMING SOLID PARTICLES

(75) Inventor: Yasumitsu Shimizu, Osaka (JP)

(73) Assignee: Sunstar, Inc., Osaka (JP)

( * ) Notice: Subject to any disclaimer, the term of this patent is extended or adjusted under 35 U.S.C. 154(b) by 0 days.

(21) Appl. No.: 09/381,226

(22) PCT Filed: Mar. 16, 1998

(86) PCT No.: PCT/JP98/01130
§ 371 (c)(1),
(2), (4) Date: Sep. 17, 1999

(87) PCT Pub. No.: WO98/41190
PCT Pub. Date: Sep. 24, 1998

(30) Foreign Application Priority Data

Mar. 18, 1997 (JP) .............................. 9-085849

(51) Int. Cl.[7] .......................... A61K 7/16; A61K 9/16; A61K 9/107; A61K 47/48; A61K 9/58

(52) U.S. Cl. ................... 424/49; 514/900; 514/902; 514/953; 514/965; 514/772.2; 424/486; 424/501; 424/426

(58) Field of Search ................ 424/49, 426, 501, 424/486; 514/900, 902, 953, 965, 772.2

(56) References Cited

U.S. PATENT DOCUMENTS

| 4,764,377 A | 8/1988 | Goodson |
| 4,780,320 A | 10/1988 | Baker |
| 5,143,934 A | 9/1992 | Lading et al. |
| 5,198,220 A | 3/1993 | Damani |
| 5,236,355 A | 8/1993 | Brizzolara et al. |
| 5,242,910 A | 9/1993 | Damanj |
| 5,620,700 A * | 4/1997 | Berggren et al. ........... 424/435 |
| 5,702,716 A | 12/1997 | Dunn et al. |
| 6,071,530 A * | 6/2000 | Polson et al. ............... 424/426 |

FOREIGN PATENT DOCUMENTS

| JP | 63 79817 | 4/1988 |
| JP | 3271219 | 12/1991 |
| JP | 5286850 | 11/1993 |
| WO | 92/00718 | 1/1992 |

* cited by examiner

Primary Examiner—Frederick Krass
Assistant Examiner—Donna Jagoe
(74) Attorney, Agent, or Firm—Birch, Stewart, Kolasch & Birch, LLP

(57) ABSTRACT

The composition for forming solid particles of the present invention comprises a biodegradable polymer, a solvent, a polyhydric alcohol, a viscosity-increasing agent, and an active drug, wherein the composition is in the form of an emulsion comprising a continuous phase rich in the polyhydric alcohol and the viscosity-increasing agent and a dispersed phase of liquid particles rich in the biodegradable polymer and the solvent, the dispersed phase being present in said continuous phase. The above composition can allow the carrier comprising an active drug to reach all corners of narrow periodontal pockets, and the carrier comprising the active drug has high retention in the periodontal pockets, whereby making it possible to maintain the active drug for a long period of time at a high concentration.

24 Claims, 5 Drawing Sheets ase carrier in a solvent, and dissolving or dispersing an active drug in the resulting solution. When such a composition is administered, the polymer solidifies as the solvent is eluted in water, and the active drug is released. Once such a polymer solidifies, however, it retains the solid form with almost no change, resulting in the possibility that the active drug is not well distributed to the bottom of deep periodontal pockets bifurcations involvement and the like. There has, therefore, been a demand for a technique for effectively delivering an active drug to portions where drug administration is difficult.

COMPOSITION FOR FORMING SOLID PARTICLES

This application is the national phase under 35 U.S.C. §371 of PCT International Application No. PCT/JP98/01130 which has an International filing date of Mar. 16, 1998 which designated the United States of America.

TECHNICAL FIELD

The present invention relates to a composition for forming solid particles. Further, the present invention relates to a therapeutic agent, a prophylactic, or the like for periodontal diseases comprising the above composition.

BACKGROUND ART

Traditionally, various studies in pharmaceutics have been made for long-term sustained-release property and retention of active drugs and the like in vivo. For example, the use of solid particles, such as microspheres, nanospheres and microcapsules, can be understood as one of the forms of such studies. However, there have been pointed out some problems involved in the production of microspheres and the like, including 1) the residue of an organic solvent used to dissolve a polymer, 2) the necessity of special equipments for their production, and the like. There has, therefore, been a demand for a method capable of safely and easily preparing microspheres and the like.

In addition, various studies on pharmaceutics have been made on delivery systems for treatment of periodontal diseases. A typical example of a solid preparation is given in U.S. Pat. No. 4,764,377. The technique disclosed therein, however, poses great burdens on both physicians and patients, including time period required for administration, necessary techniques for administration, and removal of fibers after a given period of time. On the other hand, as to semi-solid preparations, there is a composition disclosed in U.S. Pat. No. 5,143,934. However, it is far from being satisfactory from the viewpoints of retention of an active drug in periodontal pockets after administration of the composition. There has, therefore, been a demand for a simple technique in which an effective concentration of the active drug can be maintained at the administration site.

Regarding the drug delivery to periodontal pockets in the treatment of a periodontal disease, some elements which have recently been regarded as pharmaceutically important include 1) administration into periodontal pockets being simple, 2) long-term retention in periodontal pockets being possible; and 3) the element acting as a carrier being biodegradable. In view of the above, one disclosed in U.S. Pat. No. 5,236,355, for example, refers to a microsphere preparation comprising an active drug. The technique disclosed herein is expensive because a complicated method known as phase separation is employed in the preparation of microspheres, making it costly, so that its clinical application seems to be difficult, in consideration of the costs involved in the present treatment of periodontal diseases. Furthermore, this preparation is in a form such that microspheres per se are administered.

Further, WO92/00718 discloses a delivery system into periodontal pockets, and U.S. Pat. No. 5,242,910 discloses an invention relating to a sustained-release composition for the treatment of a periodontal disease with nearly the same pharmaceutical characteristics as those of the aforementioned delivery system. The compositions for the treatment of a periodontal disease disclosed in these publications are all obtained in such a state of dissolving a polymer (biodegradable polymer) functioning as a sustained-release Also, as described in U.S. Pat. No. 4,780,320, as to the preparation retained in the pocket, controlling the preparation so as not to be present in an exceeding length of time is considered to be an important factor. Therefore, in the design of a preparation, it is considered to be necessary to come up with a solution, including enlarging the surface area of the solidified polymer compound in order to increase the biodegradability of the element used as a carrier.

A first object of the present invention is to provide a composition for forming solid particles in which the administration procedures are simple, an effective concentration of the active drug can be maintained at the administration site, so that the active drug can be effectively delivered to sites difficult in administration. Still a second object of the present invention is to provide a method for safely and easily manufacturing the solid particles. Still a third object of the present invention is to provide a therapeutic agent and a prophylactic agent comprising the composition for a periodontal disease, and the like. Still a fourth object of the present invention is to provide a method of treatment and a prophylactic method effective for a periodontal disease, and the like using the above composition. These and other objects of the present invention will be apparent from the following description.

DISCLOSURE OF INVENTION

The gist of the present invention pertains to:

[1] a composition for forming solid particles comprising a biodegradable polymer, a solvent, a polyhydric alcohol, a viscosity-increasing agent, and an active drug, wherein said composition is in the form of an emulsion comprising a continuous phase rich in the polyhydric alcohol and the viscosity-increasing agent and a dispersed phase of liquid particles rich in the biodegradable polymer and the solvent, the dispersed phase being present in the continuous phase;

[2] a method for manufacturing a composition for forming solid particles, comprising adding an active drug to a mixture comprising a polyhydric alcohol and a viscosity-increasing agent and/or to a biodegradable polymer dissolved with a solvent, and mixing the mixture comprising a polyhydric alcohol and a viscosity-increasing agent, and the biodegradable polymer dissolved with a solvent;

[3] a therapeutic agent or prophylactic agent of a periodontal disease or gingivitis, comprising the composition of item [1] above;

[4] a method of treatment or prophylactic method of a periodontal disease or gingivitis comprising administering a sufficient amount of the composition of item [1] above to a periodontal pocket for the treatment or prophylaxis of a periodontal disease or gingivitis; and

[5] the use of the composition of item [1] above for manufacturing a therapeutic agent or prophylactic agent of a periodontal disease or gingivitis.

BEST MODE FOR CARRYING OUT THE INVENTION

Figure 1:
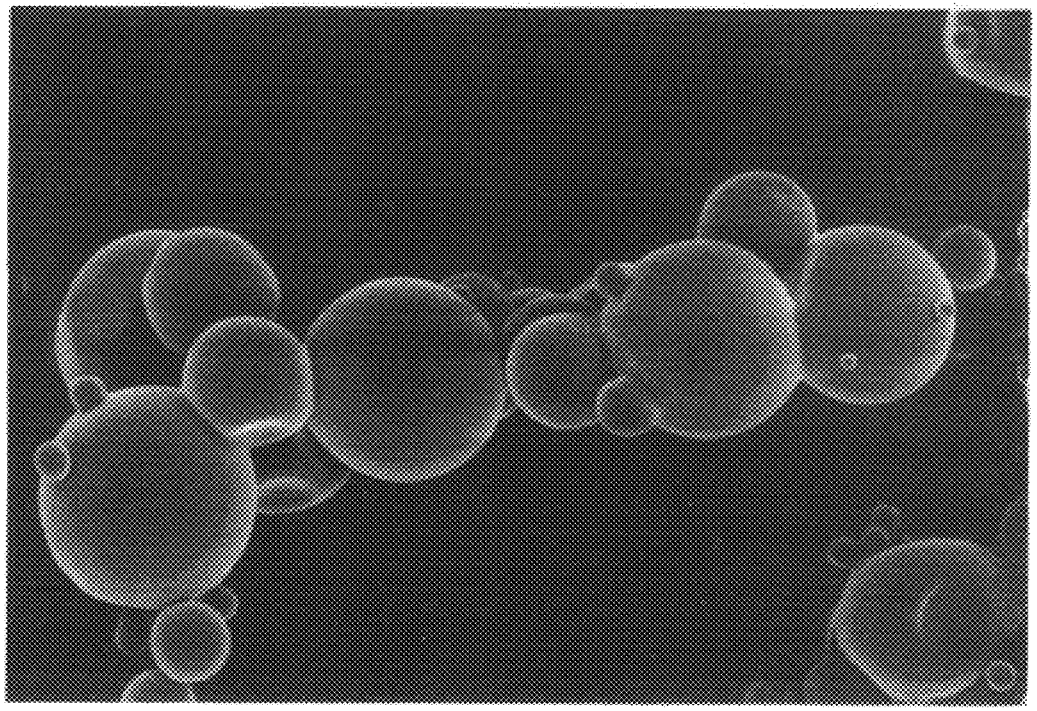
FIG. 1 is a view showing solid particles rich in poly (lactide-co-glycolide), wherein the magnification of this image (scanning electron microscope) is 3,000.

1. Composition of the Present Invention for Forming Solid Particles

The composition of the present invention for forming solid particles comprises a biodegradable polymer, a solvent, a polyhydric alcohol, a viscosity-increasing agent, and an active drug, wherein the composition is in the form of an emulsion comprising a continuous phase rich in the polyhydric alcohol and the viscosity-increasing agent and a dispersed phase of liquid particles rich in the biodegradable polymer and the solvent, the dispersed phase being present in the continuous phase.

The biodegradable polymer usable in the composition of the present invention for forming solid particles is not particularly limited, as long as it is hydrolyzable non-enzymatically or enzymatically. Concretely, such biodegradable polymers include polylactic acids, polyglycolic acids, poly(lactide-co-glycolides), polycaprolactones, polyamides, polyurethanes, polyanhydrides, polyesteramides, poly(malic acids), chitin, and chitosan, with preference given to polylactic acids, polyglycolic acids, and poly(lactide-co-glycolides) from the viewpoint of the compatibility in periodontal pockets. The biodegradable polymer may be constituted by a single ingredient alone or a mixture of two or more kinds of ingredients.

In addition, from the viewpoints of the formability of the solid particles formed in periodontal pockets and the dispersibility of the solid particles in periodontal pockets, it is preferable that the biodegradable polymer for the present invention is ones showing appropriate viscosity. Concretely, the intrinsic viscosity of the biodegradable polymer is preferably in the range of from 0.075 to 0.210 dl/g, more preferably in the range of from 0.100 to 0.150 dl/g. In addition, the molecular weight of the biodegradable polymer is not particularly limited, and the weight-average molecular weight is preferably in the range of from 2,000 to 50,000, more preferably in the range of from 5,000 to 20,000.

The solvent usable in the composition of the present invention is not particularly limited, as long as it readily dissolves the biodegradable polymer without affecting the degradability thereof. Concretely, the solvents include triethyl citrate, propylene carbonate, N-methyl-2-pyrrolidone and glyceryl triacetate, with preference given to triethyl citrate and glyceryl triacetate. The solvent may be constituted by a single ingredient alone or a mixture of two or more kinds of ingredients.

As the polyhydric alcohols usable for the composition of the present invention, there can be selected those which do not affect the degradability of the biodegradable polymer and which easily dissolve the viscosity-increasing agent used, with preference given to dihydric and trihydric alcohols. Concretely, the polyhydric alcohols include glycerol, ethylene glycol, diethylene glycol, propylene glycol, hexylene glycol, 1,5-pentanediol, and 1,3-butylene glycol, with preference given to glycerol and propylene glycol. The polyhydric alcohol may be constituted by a single ingredient alone or a mixture of two or more kinds of ingredients.

As the viscosity-increasing agents usable for the composition of the present invention, there can be selected those which dissolve in the polyhydric alcohol with heating or without heating, have high biological compatibility, and are stable in its preparation. Concretely, the viscosity-increasing agents include polyvinyl alcohols, polyvinyl pyrrolidones, gelatin, collagen, proteins, polyalbumins, carrageenan, guar gum, hydroxyethyl cellulose, xanthane gum, and tragacanth gum, with preference given to gelatin and hydroxyethyl cellulose. The viscosity-increasing agent may be constituted by a single ingredient alone or a mixture of two or more kinds of ingredients.

The active drug usable in the composition of the present invention for forming solid particles cannot be absolutely defined because it varies depending on the diseases to be treated. When the composition of the present invention is used in, for instance, the area of dentistry, it is not particularly limited, as long as it has properties of preventing infection in a periodontal tissue, mitigating an extent of inflammation, effectively acting on regeneration of a periodontal tissue, or the like, and is medically acceptable. The active drugs include, for example, antibiotics, antibacterial agents, antifungal agents, anti-inflammatory agents, growth factors, antitumor agents, analgesics, anesthetics, vaccines, medicines for central nervous, hormones, antihistamines, and anti-ulcer agents, and the like. More concretely, the antibiotics include tetracycline antibiotics and macrolide antibiotics, including minocycline hydrochloride, tetracycline, doxycycline, erythromycin, clarithromycin, and the like. Further, there can be used antibiotics such as metronidazole. The antibacterial agents include quaternary ammonium salts, such as cetyl pyridinium chloride; bisguanides, such as chlorhexidine; new quinolone, such as sparfloxacin and ofloxacin; triclosan, and the like. In addition, the antifungal agents include miconazole nitrate, trichomycin, and azalomycine. The anti-inflammatory agents include ibuprofen, flurbiprofen, aspirin, indomethacin, dexamethasone, and hydrocortisone. The growth factors include platelet-derived growth factors, epidermal growth factors, fibroblast growth factors, insulin-like growth factors, and the like. The active drug may be constituted by a single ingredient alone or a mixture of two or more kinds of ingredients.

The content of each ingredient described above is not particularly limited, as long as the emulsion comprising a continuous phase and a dispersed phase can be stably present. More preferred content ranges are as follows:

The content of the biodegradable polymer is preferably from 1.0 to 30% by weight, more preferably from 2.0 to 10% by weight, of the composition of the present invention. The content of the biodegradable polymer is preferably 1.0% by weight or more, from the viewpoint of retaining an effective amount of the active drug, and the content is preferably 30% by weight or less, from the viewpoint of reaching a sufficient amount of active drug released.

The content of the solvent is preferably from 5.0 to 40% by weight, more preferably from 10 to 25% by weight, of the composition of the present invention. The amount of the polymer which can be dissolved decreases with the decrease in the amount of the solvent, and the content of the solvent is preferably 5.0% by weight or more, from the viewpoint of retaining an effective amount of the active drug, and the content is preferably 40% by weight or less, from the viewpoint of the stability of the emulsion.

The content of the polyhydric alcohol is preferably from 30 to 90% by weight, more preferably from 40 to 90% by weight, still more preferably from 50 to 90% by weight, and particularly preferably from 55 to 75% by weight, of the composition of the present invention. The content of the polyhydric alcohol is preferably 30% by weight or more, from the viewpoint of the stability of the emulsion, and the content is preferably 90% by weight or less, from the viewpoints of the retention of the active drug and the stability of the emulsion.

The content of the viscosity-increasing agent is preferably from 0.05 to 10% by weight, more preferably from 0.1 to 5.0% by weight, and particularly preferably from 1.0 to 5.0% by weight, of the composition of the present invention. The content of the viscosity-increasing agent is preferably 0.05% by weight or more, from the viewpoint of increasing viscosity of the continuous phase to stabilize the emulsion, and the content is preferably 10% by weight or less, from the viewpoint of suppressing the influence to the emulsion by the increase in viscosity of the continuous phase.

The content of the active drug is not particularly limited, as long as it is at a level where the desired effect can be exhibited, and the content is preferably from 0.1 to 20% by weight, more preferably from 0.5 to 10% by weight, and particularly preferably from 0.5 to 5% by weight, of the composition of the present invention. The content of the growth factor is more preferably about one-tenth of these amounts. In any case, from the viewpoint of effectiveness, the active drug is preferably contained in an amount of the lower limit or more, and even when the active drug is contained in an amount of the upper limit or more, the effectiveness is not increased.

Also, the total amount of the polyhydric alcohol and the viscosity-increasing agent is preferably from 40 to 95% by weight, more preferably from 45 to 80% by weight, and particularly preferably from 65 to 80% by weight, of the composition of the present invention. The total amount is preferably 40% by weight or more, from the viewpoint of the stability of the emulsion, and the total amount is preferably 95% by weight or less, from the viewpoints of the stability of the emulsion and the retention of the active drug.

In addition, there can be added pharmacologically acceptable additives, such as magnesium chloride, magnesium sulfate, magnesium carbonate, calcium chloride, and barium chloride, to the composition of the present invention. The content of these additives is preferably from 1.0 to 30% by weight, more preferably from 1.0 to 25% by weight, and particularly preferably from 1.0 to 10% by weight, of the composition of the present invention.

The composition of the present invention is in the form of an emulsion comprising a continuous phase rich in a polyhydric alcohol and a viscosity-increasing agent and a dispersed phase of liquid particles rich in a biodegradable polymer and a solvent, the dispersed phase being present in the continuous phase.

The average particle size of the liquid particles is preferably from 1 to 300 $\mu$m, more preferably from 1 to 50 $\mu$m, particularly preferably from 5 to 40 $\mu$m, and most preferably from 5 to 25 $\mu$m, as observed by phase-contrast microscope. The average particle size is preferably 1 $\mu$m or more, from the viewpoint of maintaining the amount of the active drug retained in each solid particle, and the average particle size is preferably 300 $\mu$m or less, from the viewpoint of the dispersibility in the periodontal pockets.

It is preferable that the composition of the present invention is those in which the ingredients of the polyhydric alcohol and the viscosity-increasing agent, which constitute the continuous phase, are allowed to quickly dissolve, whereby forming solid particles rich in a biodegradable-polymer having low solubility against water, when the composition is brought into contact with an aqueous component (e.g., an aqueous component in the oral cavity). Because the above solid particles incorporate surrounding ingredients, such as the active drug, during their formation (including during the formation of liquid particles), the solid particles contain the active drug. Because the above solid particles are small and have high fluidity, solid particles containing the active drug are expected to be distributed well into all corners of periodontal pockets, when their behavior in periodontal pockets is considered. The average particle size of the solid particles formed is not particularly limited, and the average particle size is preferably from 1 to 100 $\mu$m, more preferably from 1 to 50 $\mu$m, and particularly preferably from 5 to 50 $\mu$m, as determined by scanning electron microscope.

In addition, in a case where the composition of the present invention is administered to a periodontal pocket, or the like, it is preferable that the fluidity of the composition is of a level which is injectable from a syringe.

Furthermore, an adhesive, such as an acrylic acid polymer or a starch derivative, may be contained in the continuous phase. In this case, the adhesiveness of the solid particles formed is even more enhanced. The above composition is preferably used when purposefully used to obtain solid particles showing high retention at the administration site. Concrete examples of the adhesives, such as acrylic acid polymers and starch derivatives, include carboxyvinyl polymers, dextrin, alpha-starch, and partial alpha-starch. The content of the adhesive in the composition comprising the adhesive is not particularly limited, and the content is preferably from 0.005 to 1.0% by weight, more preferably from 0.01 to 0.5% by weight, of the composition for forming solid particles. The adhesive may be constituted by a single ingredient alone or a mixture of two or more kinds of ingredients.

In addition, in the composition of the present invention, the active drug is usually contained in both the continuous phase and the dispersed phase which comprises liquid particles, and the extent of the content of the active drug in the two phases depends on its affinity for the ingredients constituting the continuous phase and the dispersed phase. Therefore, the effective amount of the active drug in the continuous phase and the dispersed phase can be adjusted by appropriately selecting the kinds and combination of the active drug, kinds and combination of individual ingredients, and the like. With the formation of the solid particles rich in a biodegradable polymer from liquid particles, the active drug is incorporated in the solid particles.

The method for manufacturing the composition of the present invention is not particularly limited, and it is preferable that the composition is prepared so as to form the above emulsion with each ingredient. For example, the composition can be obtained by mixing a mixture comprising a polyhydric alcohol and a viscosity-increasing agent with a biodegradable polymer dissolved with a solvent. When the ingredients of the continuous phase and the ingredients of the dispersed phase are mixed, it is preferable that both phases are maintained at a temperature of about 50° to about 60° C. under an appropriate stirring force. By maintaining the temperature as described above, the apparent viscosity is reduced, whereby producing a state in which their mixing is facilitated. In addition, when the polyhydric alcohol and the viscosity-increasing agent are mixed, the polyhydric alcohol may be heated to a temperature of 80° to 140° C.

According to the characteristics thereof, the active drug may be added to the ingredients of either phase before these ingredients are mixed. For instance, there may be exemplified an embodiment of mixing a mixture of a polyhydric alcohol, a viscosity-increasing agent, and an active drug with a biodegradable polymer dissolved with a solvent; an embodiment of mixing a mixture of a polyhydric alcohol and a viscosity-increasing agent with a mixture of a biodegradable polymer dissolved with a solvent and an active drug; an embodiment of adding an active drug to both phases, and then mixing the two phases, and the like. In addition, when the active drug is added to the ingredients of the continuous phase, it may be added during heating, or it may be added after cooling, depending on the characteristics of the active drug. In addition, when an adhesive is used, these ingredients are added to the ingredients of the continuous phase to allow dissolution of the adhesive, and the ingredients may, for example, be heated to a temperature of 50° to 140° C.

2. Therapeutic Agent, Prophylactic Agent, Methods of Treatment, and Prophylactic Method of the Present Invention.

Since solid particles comprising an active drug can be obtained, the, composition of the present invention for forming solid particles can be utilized in medicinal fields. It is, therefore, possible to provide a therapeutic agent, a prophylactic agent, a method of treatment, and a prophylactic method for various diseases by using the composition of the present invention. In the field of dentistry, in particular, the composition of the present invention can, for example, be preferably used for the treatment of a periodontal disease, treatment of gingivitis, prophylaxis of periodontal diseases, and prophylaxis of gingivitis.

When the composition of the present invention is used in the therapeutic method and the prophylactic method, the composition of the present invention per se may be used, or a suspension of solid particles formed by adding water and the like to the composition may be used. The above suspension can be administered by various administration methods, such as oral administration, subcutaneous injection, and intravenous injection. When the composition of the present invention per se is used, as in the case where the composition is administered into a periodontal pocket, solid particles are formed by an aqueous component such as saliva or gingival crevicular fluid.

As the method of treatment or the prophylactic method of the present invention, there can be exemplified the following embodiments in the field of dentistry.

(1) A method of treatment of a periodontal disease or gingivitis comprising administering a sufficient amount of the composition of the present invention to a periodontal pocket for the treatment of a periodontal disease or gingivitis.

(2) A prophylactic method of a periodontal disease or gingivitis comprising administering a sufficient amount of the composition of the present invention to a periodontal pocket for the prophylaxis of a periodontal disease or gingivitis.

In these method of treatment and prophylactic method in the field of dentistry, the amount of the composition of the present invention used is an amount sufficient for eliminating pathological bacteria in a case where an antibacterial agent, and the like is used as an active drug. The usage is one administration in one to two weeks, and the number of administration is preferably once or twice. The administration amount of the composition for forming solid particles to a periodontal pocket is preferably an amount such that the periodontal pocket is full of the composition (about 50 mg).

As described above, since the composition of the present invention can be used for the method of treatment and the prophylactic method for a periodontal disease or gingivitis, the composition of the present invention can be used for a therapeutic agent for a periodontal disease or gingivitis, or a prophylactic agent for a periodontal disease or gingivitis. In the above therapeutic agent and the prophylactic agent of the present invention, minocycline hydrochloride is preferable as an active drug from the viewpoint of sterilization and bacteriostatis of the periodontpathic bacteria which is considered to be the causation of such diseases.

Further, the present invention provides the use of the composition for forming solid particles for manufacturing a therapeutic agent or prophylactic agent for a periodontal disease or gingivitis.

The present invention will be described in further detail below by means of Examples, Comparative Examples, and Test Examples, but the present invention is by no means limited by these Examples, and the like.

Example 1

A composition for forming solid particles was prepared by using each of the following ingredients in the composition below.

| | |
|---|---|
| Minocycline Hydrochloride | 10% by weight (potency) |
| Poly(lactide-co-glycolide) [50/50 (weight ratio), intrinsic viscosity 0.130 dl/g, weight-average molecular weight 10,000] | 10% by weight |
| Triethyl Citrate | 10% by weight |
| Gelatin | 0.1% by weight |
| Dextrin | 0.05% by weight |
| Magnesium Chloride | 20% by weight |
| Concentrated Glycerol | Balance |

Magnesium chloride, gelatin, and dextrin were dispersed in concentrated glycerol, and the mixture was heated to dissolve the ingredients. After cooling, minocycline hydrochloride was allowed to be dispersed and dissolved. On the other hand, a poly(lactide-co-glycolide) was dissolved in triethyl citrate. With maintaining the both mixtures at a temperature of 50° to 60° C., a triethyl citrate solution was added to a concentrated glycerol solution, and the resulting mixture was uniformly mixed to give a desired composition. This composition was observed with an optical microscope, and as a result, there were confirmed liquid particles having a particle size of about 5 to about 15 μm.

The composition for forming solid particles as prepared above was suspended in distilled water to form solid particles rich in a poly(lactide-co-glycolide). The resulting suspension was centrifuged, and the formed solid particles were separated. The separated particles were washed twice with distilled water. Subsequently, the particles were suspended in a small amount of distilled water, and this suspension was lyophilized. The resulting lyophilized solid particles rich in a poly(lactide-co-glycolide) were observed with scanning electron microscope. As a result, it was found that the solid particles had a size of about 5 to about 25 μm in diameter (average size: 12.5 μm). FIG. 1 is a photograph showing the solid particles rich in the poly(lactide-co-glycolide) by scanning electron microscope.

Example 2

A composition for forming solid particles was prepared in the same manner as in Example 1 by using each of the following ingredients in the composition below.

| Minocycline Hydrochloride | 10% by weight (potency) |
|---|---|
| Poly(lactide-co-glycolide) [50/50 (weight ratio), intrinsic viscosity 0.130 dl/g, weight-average molecular weight 10,000] | 10% by weight |
| Triethyl Citrate | 10% by weight |
| Gelatin | 0.5% by weight |
| Magnesium Chloride | 20% by weight |
| Concentrated Glycerol | Balance |

This composition was observed with an optical microscope, and as a result, there were confirmed that liquid particles had a size of about 5 to about 15 μm in diameter. In addition, the solid particles obtained by treating the composition in the same manner as in Example 1 were observed, and as a result, it was found that the solid particles had a size of about 10 to about 30 μm in diameter (average size: 20 μm).

Example 3

A composition for forming solid particles was prepared in the same manner as in Example 1 by using each of the following ingredients in the composition below.

| Minocycline Hydrochloride | 2.0% by weight (potency) |
|---|---|
| Poly(lactide-co-glycolide) [75/25 (weight ratio), intrinsic viscosity 0.132 dl/g, weight-average molecular weight 10,000] | 3.5% by weight |
| Triethyl Citrate | 13.5% by weight |
| Gelatin | 1.5% by weight |
| Magnesium Chloride | 5.0% by weight |
| Concentrated Glycerol | Balance |

This composition was observed with an optical microscope, and as a result, there were confirmed that liquid particles had a size of about 5 to about 15 μm in diameter.

Figure 2:
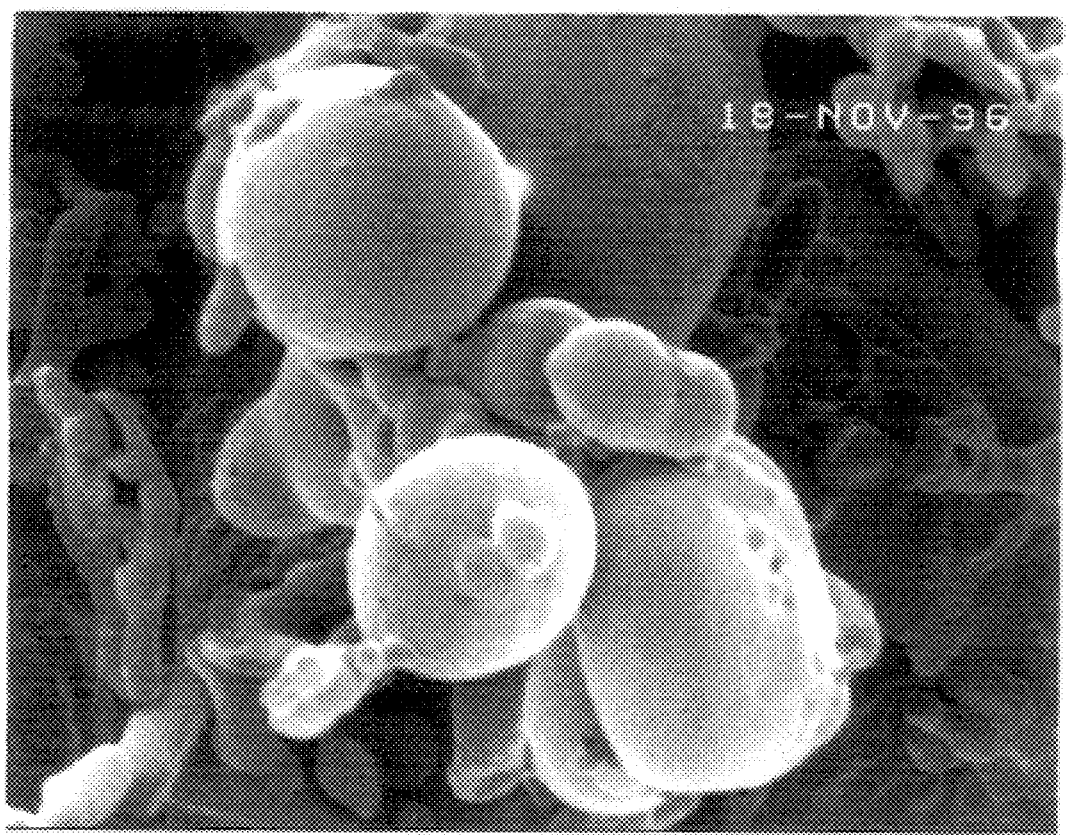
FIG. 2 is a view showing solid particles rich in poly (lactide-co-glycolide), wherein the magnification of this image (scanning electron microscope) is 900.

In addition, the solid particles obtained by treating the composition in the same manner as in Example 1 were observed, and as a result, it was found that the solid particles had a size of about 10 to about 30 μm in diameter (average size: 20 μm). FIG. 2 is a photograph showing the solid particles rich in the poly(lactide-co-glycolide) by scanning electron microscope.

Examples 4 to 12

(1) Biodegradable Polymer and Solvent

A triethyl citrate solution comprising a poly(lactide-co-glycolide) [50/50 (weight ratio), intrinsic viscosity 0.130 dl/g, weight-average molecular weight 10,000] in an amount of 50% by weight was prepared.

(2) Polyhydric Alcohol, Viscosity-Increasing Agent, and Active Drug

Gelatin to be dissolved was added to concentrated glycerol heated to a temperature of about 100° C., and the mixture was then cooled. The concentration of the gelatin A was adjusted to 3.0% by weight. After cooling, minocycline hydrochloride was added so as to have a final concentration of 2% by weight (potency).

Subsequently, the composition for forming solid particles was prepared by mixing (1) a triethyl citrate solution and (2) a glycerol solution.

The mixing of (1) and (2) was carried out at a weight ratio of 5:95, 10:90, 20:80, 30:70, 40:60, 50:50, 60:40, 70:30, and 80:20, respectively.

Examples 13 to 18

(1) Biodegradable Polymer and Solvent

A triethyl citrate solution comprising a poly(lactide-co-glycolide) [50/50 (weight ratio), intrinsic viscosity 0.130 dl/g, weight-average molecular weight 10,000] in an amount of 50% by weight was prepared.

(2) Polyhydric Alcohol, Viscosity-Increasing Agent, and Active Drug

Magnesium chloride and gelatin were added to concentrated glycerol heated to a temperature of about 100° C. Further, either one of dextrin (Example 13), carboxyvinyl polymer (Example 14), xanthane gum (Example 15), guar gum (Example 16), and pectin (Example 17) was added to be dissolved therein. The concentration of the gelatin was adjusted to 3.0% by weight, and the concentration of dextrin, or the like was adjusted to 0.1% by weight. In addition, an example where dextrin, or the like was not added was referred to as Example 18. After cooling, minocycline hydrochloride was added so as to have a final concentration of 2% by weight (potency).

Subsequently, the composition for forming solid particles was prepared by mixing (1) a triethyl citrate solution and (2) a glycerol solution at a weight ratio of 20:80.

Example 19

A composition for forming solid particles was prepared in the same manner as in Example 1 by using each of the following ingredients in the composition below.

| Cetylpyridinium chloride | 5.0% by weight |
|---|---|
| Propylene carbonate | 20% by weight |
| Polycaprolactone (intrinsic viscosity 0.100 dl/g, weight-average molecular weight 7,500) | 5.0% by weight |
| Hydroxyethyl Cellulose | 2.0% by weight |
| Propylene Glycol | Balance |

The resulting composition was observed with an optical microscope, and as a result, there were confirmed that liquid particles had a size of about 10 to about 20 μm in diameter. In addition, the solid particles obtained by treating the composition in the same manner as in Example 1 were observed, and as a result, it was found that the solid particles had a size of about 30 to about 40 μm in diameter (average size: 35 μm).

Example 20

A composition for forming solid particles was prepared in the same manner as in Example 1 by using each of the following ingredients in the composition below.

| | |
|---|---|
| Flurbiprofen | 1.0% by weight |
| Polylactic Acid (intrinsic viscosity 0.087 dl/g, weight-average molecular weight 5,000) | 10% by weight |
| Glyceryl Triacetate | 25% by weight |
| Gelatin | 2.5% by weight |
| Concentrated Glycerol | Balance |

The resulting composition was observed with an optical microscope, and as a result, there were confirmed that liquid particles had a size of about 10 to about 20 μm in diameter. In addition, the solid particles obtained by treating the composition in the same manner as in Example 1 were observed, and as a result, it was found that the solid particles had a size of about 25 to about 40 μm in diameter (average size: 30 μm).

Comparative Example 1

A composition shown below was prepared using each of the following ingredients.

| | |
|---|---|
| Minocycline Hydrochloride | 2% by weight (potency) |
| Poly(lactide-co-glycolide) [50/50 (weight ratio), intrinsic viscosity 0.130 dl/g, weight-average molecular weight 10,000] | 48% by weight |
| Glyceryl Triacetate | Balance |

A poly(lactide-co-glycolide) was dissolved in glyceryl triacetate, and minocycline hydrochloride was dispersed thereinto, to give a composition. This composition was uniform gel, and when this composition was observed with an optical microscope, liquid particles could not be confirmed.

Comparative Example 2

A composition shown below was prepared using each of the following ingredients.

| | |
|---|---|
| Minocycline Hydrochloride | 2% by weight (potency) |
| Polylactic Acid (intrinsic viscosity 0.122 dl/g, weight-average molecular weight 10,000) | 70% by weight |
| N-Methyl-2-pyrrolidone | Balance |

A polylactic acid was dissolved in N-methyl-2-pyrrolidone, and thereinto was dispersed minocycline hydrochloride, to give a composition. This composition was uniform gel, and when this composition was observed with an optical microscope, liquid particles could not be confirmed.

Test Example 1

Each of the compositions for forming solid-particles of Example 1, Example 3, and Comparative Example 1 was administered to 30 subjects to have periodontal pockets with 6 to 10 mm, each composition being administered to a group of 10 subjects with a root canal syringe to study on the retention of minocycline hydrochloride within the periodontal pockets. Prior to administration, each subject received scaling and root planing. The gingival crevicular fluid (GCF) was collected with paper strips 7 days after administration, and 10 days after administration, and the amounts of minocycline hydrochloride contained therein were determined. A subject where minocycline hydrochloride was present at a concentration of 0.1 μg or more in 1 ml of GCF was considered to be a case for detection. The results are shown in Table 1.

TABLE 1

| | Detection Percentage (%) | |
|---|---|---|
| | After 7 Days | After 10 Days |
| Example 1 | 100 | 87.5 |
| Example 3 | 100 | 80 |
| Comparative Example 1 | 70 | 30 |

It is found from the above results that in the preparations of Example 1 and Example 3, an effective amount of the active drug is detected from 80% of the subjects even after 10 days, which is extremely high value as compared to that of Comparative Example. This is presumably because after the active drug in the present invention is administered in the form of preparation, fine solid particles are formed, and the formed solid particles surely reach and are retained even the bottom of the pockets. In a case where the composition of Example 3 was used, there were confirmed that the concentrations of minocycline hydrochloride at which the composition can sufficiently be sterilized or subjected to bacteriostatis against periodontpathic bacteria were at a level of about 240 μg/ml after 7 days and about 80 μg/ml after 10 days. In addition, in a case where the composition of Example 1 was used, there were confirmed that the concentrations of minocycline hydrochloride were at a level of 420 μg/ml and 190 μg/ml, respectively. These results suggest that the concentration of the retained active drug was remarkably improved when a composition formulated with an adhesive was used. This is presumably because the adhesive strength of the formed solid particles are improved by the formulation of the adhesive, which in turn results in an increase in the retention of the solid particles within the periodontal pockets.

Test Example 2

Figure 3:
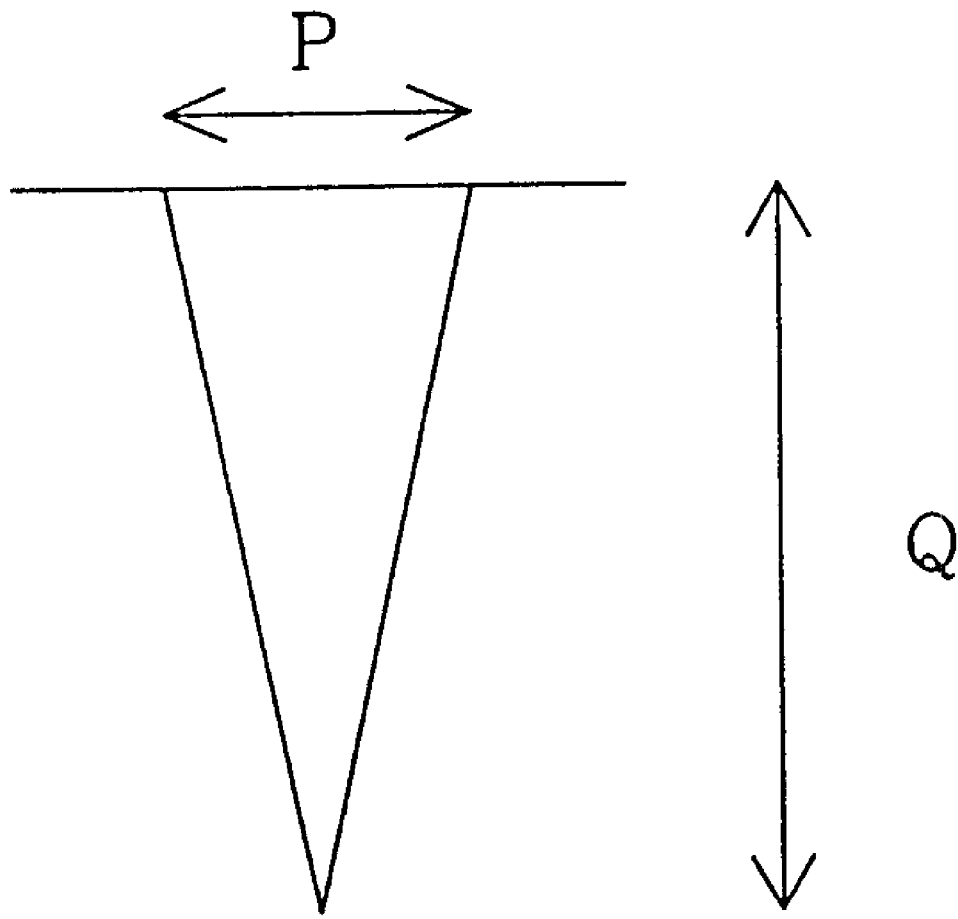
FIG. 3 shows the shape of a cavity used in Test Example 2, wherein a width P of the cavity is 6 mm, and a depth Q of the cavity is 30 mm.
Figure 4:
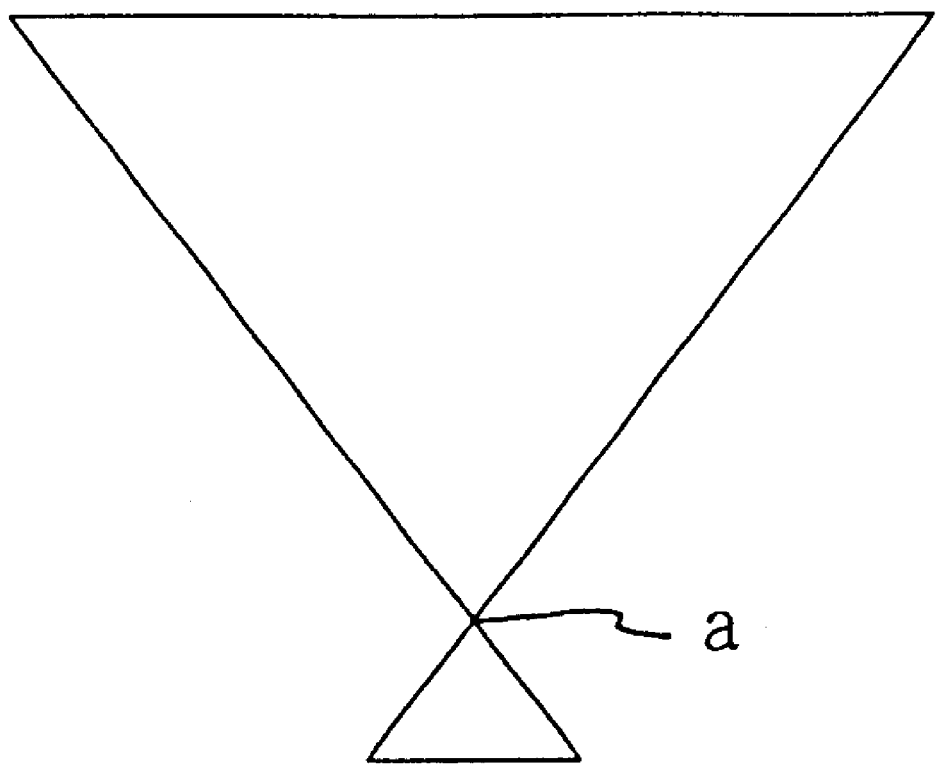
FIG. 4 is a schematic view of a vessel prepared with a dialysis tube used in Test Example 4. In the figure, "a" is a knot portion of the dialysis tube.

In order to study the reachability of the solid particles released from the composition for forming solid particles to a narrow gap such as a bottom of a periodontal pocket, an in vitro test was carried out. A model having a cavity as shown in FIG. 3 was prepared from agar. The periphery of the cavity and the agar was filled with phosphate buffer, and each of the compositions of Example 1, Example 3, Comparative Example 1, and Comparative Example 2 was poured from a top with a root canal syringe. The reachability of the composition to the bottom was determined by visual observation and by detecting minocycline hydrochloride at the bottom. The results are shown in Table 2.

TABLE 2

| | Example 1 | Example 3 | Comp. Example 1 | Comp. Example 2 |
|---|---|---|---|---|
| Distance Reached from Top (mm) | 30 | 30 | 16 | 17 |

TABLE 2-continued

| | Example 1 | Example 3 | Comp. Example 1 | Comp. Example 2 |
|---|---|---|---|---|
| Minocycline Hydrochloride | Detected*[1] | Detected*[1] | Not Detected | Not Detected |

Note *[1]Greater than 0.1 μg/ml.

It was found from Table 2 that the compositions for forming solid particles of the present invention could allow to spread the solid particles released from the composition to all corners to reach even a small gap.

Sanko Junyaku K. K., fractional molecular weight 12,000 to 14,000), and dialyzed against 100 ml of phosphate buffer at 37° C. for 48 hours to determine the amount of minocycline hydrochloride in the fluid out of the dialysis tube. From the amount of minocycline hydrochloride contained in the composition for forming solid particles prior to dialysis and the amount of minocycline hydrochloride in the fluid out of the dialysis tube, the proportion of minocycline hydrochloride retained in the dialysis tube, i.e. the proportion of minocycline hydrochloride included in the solid particles, was calculated.

The results are shown in Table 3.

TABLE 3

| | Compositional Ratio (% by weight) | | | | | | | | |
|---|---|---|---|---|---|---|---|---|---|
| Constituents for Dispersed Phase | 5 | 10 | 20 | 30 | 40 | 50 | 60 | 70 | 80 |
| Constituents for Continuous Phase | 95 | 90 | 80 | 70 | 60 | 50 | 40 | 30 | 20 |
| Total | 100 | 100 | 100 | 100 | 100 | 100 | 100 | 100 | 100 |
| Stability | ○ | ◎ | ◎ | ◎ | ◎ | ○ | X | X | X |
| of | | | | | | | | | |
| Emulsion | ○ | ◎ | ◎ | ◎ | ◎ | ○ | X | X | X |
| Retentiveness | <10 | 16 | 32 | 40 | 63 | 75 | NT | NT | NT |
| of | | | | | | | | | |
| Medicament (%) | <10 | 16 | 32 | 40 | 63 | 75 | NT | NT | NT |

Note):
NT: No test was carried out because a stable emulsion was not formed.

Test Example 3

The compositional ratio of the biodegradable polymer and the solvent to the polyhydric alcohol and the viscosity-increasing agent was studied. With respect to each of the compositions for forming solid particles obtained in Examples 4 to 12, there were confirmed the stability of emulsion and the retention of the active drug in the solid particles.

The stability of emulsion was evaluated by allowing the present composition to stand at 40° C. for one month, and observing the properties of the composition visually and with a microscope. The properties of the present compositions were observed with the principal object to determine whether or not two-phase separation takes place, and whether or not the state of emulsion is maintained as follows:

◎: No two-phase separation took place, and the emulsion was present in a stable form.

o: Either a tendency of the two-phase separation or reduction of emulsion was observed.

x: Both the tendency of the two-phase separation and the reduction of emulsion were observed.

The retention of the active drug was evaluated as follows.

An about 0.1 g of the composition for forming solid particles was placed in a dialysis tube (manufactured by It was found from Table 3 that in a case where the proportion of the continuous phase to the dispersed phase was in an extreme, the stability of emulsion tended to be lowered. Particularly in a case where the continuous phase was small, the formation of emulsion per se did not take place. In addition, by increasing the proportion of the dispersed phase, there was confirmed a tendency that the amount of the active drug included into the solid particles could be made large.

Test Example 4

With respect to each of the compositions for forming solid particles prepared in Examples 13 to 18, the formed solid particles were tested for the retention. The evaluation for the retention was carried out as follows. A vessel as shown in FIG. 4 was prepared using a dialysis tube (Commercial Product No. UC-16-32-100, manufactured by Sanko Junyaku K. K.). As shown in FIG. 4, one end of the dialysis tube is closed.

Thereinto was placed about 100 mg of the composition, and to the composition was immediately added dropwise about 50 μl of distilled water. Subsequently, this vessel was allowed to float on a water surface of the water tank filled with distilled water so as not to have water enter into the vessel. Five minutes or 10 minutes thereafter, the vessel was faced upside down in water so as to allow distilled water in the water tank to enter into the vessel. For 30 minutes, a state in which one non-closing end of the dialysis tube was faced downward was maintained. Thereafter, the vessel was dried, and the retention of the solid particles was evaluated by a weight change. The results are shown in Table 4.

TABLE 4

| | Retention Rate (%) | |
| --- | --- | --- |
| | After 5 min. | After 15 min. |
| Composition for Forming Solid Particles | | |
| Example 13 | 3.16 | 13.85 |
| Example 14 | 2.84 | 10.53 |
| Example 15 | 0.91 | 0.68 |
| Example 16 | 0.52 | 0.61 |
| Example 17 | — | 0.58 |
| Example 18 | 0.22 | 0.42 |

The retention rate was obtained as follows. Specifically, an increased amount in the weight of the dialysis tube was considered as the amount of the solid particles retained in the vessel, and the amount was divided by the amount of the composition placed in the vessel. The resulting value was expressed as percentage, and referred to as the retention rate. It is clear from the above results that in a case where dextrin or carboxyvinyl polymer was added, both the retention after 5 minutes and after 15 minutes were high.

Test Example 5

Figure 5:
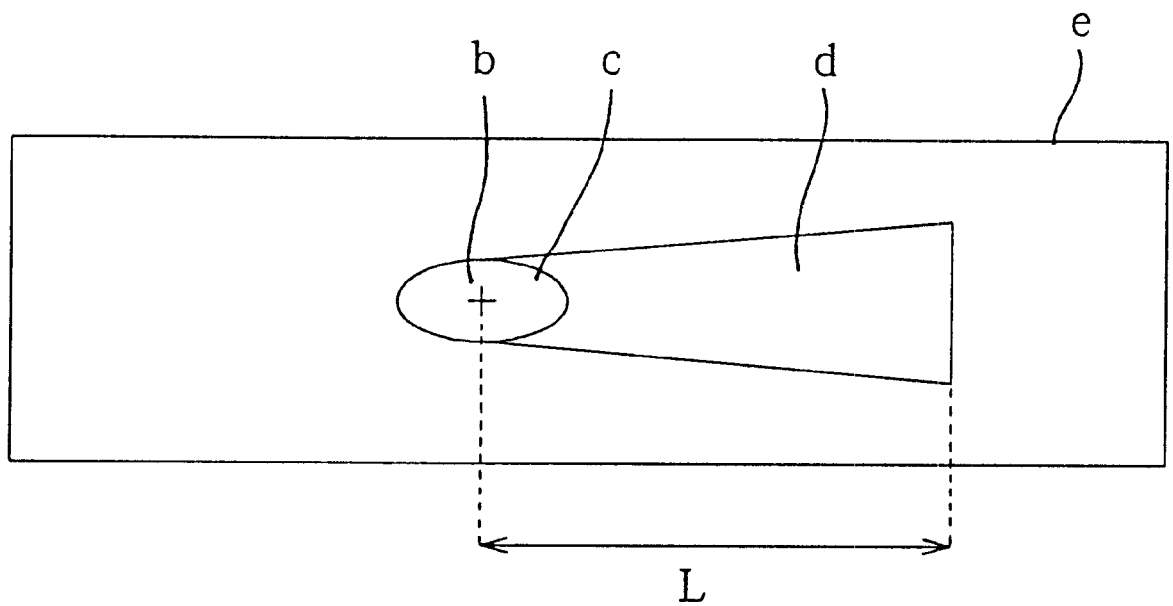
FIG. 5 is a schematic view showing the positions of a center "b" of a fixed position, the fixed position "c", a spreading area "d" of solid particles, and a distance L of the spreading area on a slide glass "e" in Test Example 5.

An in vitro test was carried out in the following manner using each of the compositions for forming solid particles prepared in Examples 13 to 18. As shown in FIG. 5, about 100 mg each of the compositions for forming solid particles was placed on a fixed position on a slide glass, and the slide glass was allowed to stand in water with an angle of about 20 degrees. After 10 minutes, the slide glass was lightly shaken sideways to remove ingredients not adhered to the slide glass. Subsequently, this slide glass was dried, and the fluidity and the retention of the solid particles were evaluated from the weight change of the slide glass before and after the test and from the spreading of the adhered solid particles (distance L toward a lower end from a center b of a fixed position).

The results are shown in Table 5.

TABLE 5

| | Weight Change (mg) | Spreading (mm) |
| --- | --- | --- |
| Composition for Forming Solid Particles | | |
| Example 13 | 9.21 | 18 |
| Example 14 | 6.72 | 30 |
| Example 15 | 3.21 | 12 |
| Example 16 | 1.55 | 8 |
| Example 17 | 0.84 | 0 |
| Example 18 | 0.51 | 0 |

It was clear from the results that in a case of the composition formulated with dextrin or carboxyvinyl polymer, the adhesiveness to the surface of the slide glass was high, and the distance of spreading was long. From the above in the compositions for forming solid particles formulated with an adhesive, both the fluidity and the retention of the formed solid particles were high, thereby having extremely preferable properties for the composition thee therapeutic and prophylactic purposes in the field of dentistry.

EQUIVALENT

Those skilled in the art will recognize, or be able to ascertain using simple routine experimentation, many equivalents to the specific embodiments of the invention described in the present specification. Such equivalents are intended to be encompassed in the scope of the following claims.

INDUSTRIAL APPLICABILITY

The composition for forming solid particles of the present invention can allow the carrier comprising an active drug to reach all corners of narrow periodontal pockets. The carrier comprising the active drug has high retention in the periodontal pockets, whereby making it possible to maintain the active drug for a long period of time at a high concentration. Therefore, there can be provided more effective method for treatment or prophylactic method for such diseases as periodontal diseases by using the above composition. In addition, the production method of the present invention is a method of simply and safely manufacturing the solid particles.

What is claimed is:

1. A composition comprising a biodegradable polymer, a solvent which dissolves the biodegradable polymer, a polyhydric alcohol, a viscosity-increasing agent, and an active drug, wherein said composition is in the form of an emulsion comprising (i) a continuous phase containing more than 50% by weight of the polyhydric alcohol and the viscosity-increasing agent, and (ii) a dispersed phase of liquid particles comprising microspheres of 1 to 300 μm average particle size containing more than 50% by weight of the biodegradable polymer and the solvent, said dispersed phase being present in said continuous phase, and wherein the total amount of the polyhydric alcohol and the viscosity-increasing agent is from 40 to 95% by weight of the total composition said polyhydric alcohol being selected from the group consisting of at least one of glycerol, ethylene glycol, diethylene glycol, propylene glycol, hexylene glycol, 1,5-pentanediol and 1,3-butylene glycol, wherein the biodegradable polymer is at least one compound selected from the group consisting of polylactic acids, poly(lactide-co-glycolides), polycaprolactones, polyamides, polyurethanes, polyanhydrides, polyesteramides, poly(malic acids), chitin and chitosan.

2. The composition according to claim 1, wherein the content of the biodegradable polymer is from 1.0 to 30% by weight; the content of the solvent is from 5.0 to 40% by weight; the content of the polyhydric alcohol is from 30 to 90% by weight; the content of the viscosity-increasing agent is from 0.05 to 10% by weight; and the content of the active drug is from 0.1 to 20% by weight.

3. The composition according to claim 1, prepared by adding the active drug to a mixture comprising the polyhydric alcohol and the viscosity-increasing agent, and/or to the biodegradable polymer dissolved with the solvent other than polyhydric alcohol; and mixing the mixture comprising the polyhydric alcohol and the viscosity-increasing agent with the biodegradable polymer dissolved with the solvent.

4. The composition according to claim 1, wherein solid particles comprising a component with a majority of the biodegradable polymer are formed when contacted with a component comprising water.

5. The composition according to claim 1, further comprising an adhesive in the continuous phase.

6. The composition according to claim 5, wherein the content of the adhesive is from 0.005 to 1.0% by weight.

7. The composition according to claim 5, wherein the adhesive is a carboxyvinyl polymer and/or dextrin.

8. The composition according to claim 1, wherein a total amount of the polyhydric alcohol and the viscosity-increasing agent is from 40 to 95% by weight.

9. The composition according to claim 1, wherein the polyhydric alcohol is at least one member selected from the group consisting of glycerol, ethylene glycol, diethylene glycol, propylene glycol, hexylene glycol, 1,5-pentanediol, and 1,3-butylene glycol.

10. The composition according to claim 1, wherein the biodegradable polymer is at least one member selected from the group consisting of polylactic acids, polyglycolic acids, poly(lactide-co-glycolides), polycaprolactones, polyamides, polyurethanes, polyanhydrides, polyesteramides, poly(malic acids), chitin, and chitosan.

11. The composition according to claim 1, wherein the solvent is at least one member selected from the group consisting of triethyl citrate, propylene carbonate, N-methyl-2-pyrrolidone, and glyceryl triacetate.

12. The composition according to claim 1, wherein the viscosity-increasing agent is at least one member selected from the group consisting of polyvinyl alcohols, polyvinyl pyrrolidones, gelatin, collagen, proteins, polyalbumins, carrageenan, guar gum, hydroxyethyl cellulose, xanthane gum, and tragacanth gum.

13. The composition according to claim 1, wherein the active drug is at least one member selected from the group consisting of antibiotics, antibacterial agents, antifungal agents, anti-inflammatory agents, growth factors, antitumor agents, analgesics, anesthetics, vaccines, medicines for central nervous, hormones, antihistamines, and anti-ulcer agents.

14. The composition according to claim 1, wherein the active drug is at least one compound selected from the group consisting of tetracycline antibiotics, quinolone antibacterial agents, and macrolide antibiotics.

15. The composition according to claim 14, wherein the quinolone antibacterial agent is sparfloxacin or ofloxacin.

16. A method for manufacturing a composition of claim 1, comprising adding an active drug to a mixture comprising a polyhydric alcohol and a viscosity-increasing agent and/or to a biodegradable polymer dissolved with a solvent, and mixing the mixture comprising a polyhydric alcohol and a viscosity-increasing agent, and the biodegradable polymer dissolved with a solvent.

17. A therapeutic agent for the treatment of periodontal disease or gingivitis, comprising the composition of claim 1.

18. The therapeutic agent according to claim 17, further comprising minocycline hydrochloride as an active drug.

19. A prophylactic agent for periodontal disease or gingivitis, comprising the composition of claim 1.

20. The prophylactic agent according to claim 19, comprising minocycline hydrochloride as an active drug.

21. A method of treatment of a periodontal disease or gingivitis comprising administering a sufficient amount of the composition of claim 1 to a periodontal pocket for the treatment of a periodontal disease or gingivitis.

22. A prophylactic method of treating a periodontal disease or gingivitis comprising administering a pharmaceutically sufficient amount of the composition of claim 1 to a periodontal pocket for the prophylaxis of a periodontal disease or gingivitis.

23. A method for manufacturing a therapeutic agent or prophylactic agent for periodontal disease or gingivitis which comprises forming said agent from a composition according to claim 1.

24. The composition according to claim 1, wherein the polyhydric alcohol is glycerol; the biodegradable polymer is a poly(lactide-co-glycolide);

the solvent is triethyl citrate;
the viscosity increasing agent is gelatin;
the active drug is a minocycline antibiotic; and
the adhesive is a carboxyvinyl polymer.

* * * * *